(12) United States Patent
Gritsch et al.

(10) Patent No.: US 8,257,622 B2
(45) Date of Patent: Sep. 4, 2012

(54) MUFFLE AND METHOD OF USING

(75) Inventors: Harald Gritsch, Gries (AT); Max Wörishofer, Teifs (AT); Christoph Zobler, Aldrans (AT); Thomas Stampfer, Feldkirch-Tosters (AT); Hans-Peter Foser, Balzers (LI)

(73) Assignee: Ivoclar Vivadent AG, Schaan (LI)

( * ) Notice: Subject to any disclaimer, the term of this patent is extended or adjusted under 35 U.S.C. 154(b) by 137 days.

(21) Appl. No.: 12/291,004

(22) Filed: Nov. 5, 2008

(65) Prior Publication Data
US 2009/0239198 A1 Sep. 24, 2009

(30) Foreign Application Priority Data

Nov. 5, 2007 (AT) .................................. A 1773/2007
Oct. 8, 2008 (EP) ..................................... 08116141

(51) Int. Cl.
*A61C 13/20* (2006.01)
(52) U.S. Cl. ................. 264/16; 249/54; 264/17; 264/19; 425/DIG. 11
(58) Field of Classification Search ..................... 249/54, 249/62; 425/DIG. 11; 264/16, 17, 19
See application file for complete search history.

(56) References Cited

U.S. PATENT DOCUMENTS

| 1,307,299 | A | * | 6/1919 | Laing ............................. 249/54 |
| 4,682,644 | A | * | 7/1987 | Ueno ............................ 164/359 |
| 4,962,909 | A | * | 10/1990 | Kohler .......................... 249/54 |
| 5,948,129 | A | * | 9/1999 | Nonami et al. ............... 65/33.1 |
| 6,302,186 | B1 | | 10/2001 | Vidal |
| 6,533,969 | B1 | * | 3/2003 | Daskalon et al. ............. 264/16 |
| 6,802,894 | B2 | * | 10/2004 | Brodkin et al. ................ 106/35 |
| 7,118,085 | B2 | * | 10/2006 | Foser et al. .................... 249/54 |
| 7,445,440 | B2 | * | 11/2008 | Pokorny et al. ............... 425/170 |
| 2004/0108610 | A1 | * | 6/2004 | Foser et al. .................... 264/16 |

FOREIGN PATENT DOCUMENTS

| DE | 202005003014 U1 | 6/2005 |
| DE | 102004013668 A1 | 10/2005 |
| DE | 202007004265 U1 | 6/2007 |
| EP | 0231773 A1 | 8/1987 |
| EP | 1093769 A1 | 4/2001 |
| EP | 1484031 A1 | 12/2004 |

\* cited by examiner

*Primary Examiner* — Yogendra Gupta
*Assistant Examiner* — Emmanuel S Luk
(74) *Attorney, Agent, or Firm* — Hodgson Russ LLP (57) ABSTRACT

The invention proposes a muffle with a pressing channel and at least one mold cavity that is coupled to the pressing channel via at least one connection channel. In this case, in order to increase the pressing pressure and to improve the intermixing of the blank material, it is proposed to arrange at least two blanks (18) side by side in the pressing channel (12).

17 Claims, 6 Drawing Sheets

MUFFLE AND METHOD OF USING

CROSS-REFERENCE TO RELATED APPLICATIONS

This application claims foreign priority benefits under 35 U.S.C. §119(a)-(d) from Austrian patent application ser. no. A 1773/2007 filed Nov. 5, 2005. In addition, this application claims foreign priority benefits under 35 U.S.C. §119(a)-(d) from European patent application ser. no. 08 116 141.5 filed Oct. 8, 2008.

TECHNICAL FIELD

The invention relates to a muffle in particular for producing ceramic dental restoration components, with a pressing channel serving to receive a press blank and with at least one mold cavity that is coupled to the pressing channel via at least one connection channel, wherein the pressing channel (12) is capable of receiving at least two press blanks (18) side by side, and in particular abutting on one another. and a method for producing ceramic dental restoration components by using the aforementioned muffle.

BACKGROUND OF THE INVENTION

A muffle for producing ceramic dental restoration components, as known for example from DE 10 2004 013 668 A1, usually comprises a pressing channel and at least one mold cavity that is coupled to the pressing channel via at least one connection channel, whereby the material of a press blank inserted into the pressing channel fills the mold cavity if a pressing force is applied and the press blank is heated, and thus provides a fired ceramic dental restoration component.

In practice, however, again and again cracks and even cavities arise in ceramic dental restoration components that impair the strength and the quality of the ceramic dental restoration component.

It has been proposed to form a press chamber with a particular cross-section in a muffle, whereby a blank material in the form of a bulk material can be filled into the press chamber and is pressed into a ceramic dental restoration component. In this case, however, air pockets can remain that cannot be completely eliminated by the pressure of the press stamp during the sintering process either.

The pressing force that is effective in the mold cavity according to the proposed solution, is comparatively low due to the shape of the pressing channel—probably due the the wall friction. Further, there is the danger that a press stamp guided in the pressing channel easily jams as a result of the particular cross-section.

OBJECTS AND SUMMARY OF THE INVENTION

Accordingly, it is the object of the invention to provide a muffle as claimed in the preamble of claim 1 and a method for producing a ceramic dental restoration component as claimed in the preamble of claim 9, with the aid of which the tendency to form cracks and cavities is considerably reduced when pressing and firing ceramic dental restoration parts in particular.

According to the invention it is provided to shape a pressing channel in such a manner that at least two press blanks can be received in the pressing channel side by side, in order to combine the large cross-section of the pressing channel with a comparatively small cross-section of the connection channel.

Apparently, the comparatively small connection channel prevents the blank material from entering the connection channel for the first moment, when the melting of the grain boundaries of the blank material begins and the blank material is still quite viscous. Only if the blank material is quite thin fluid due to further melting, the blank material overcomes the "barrier" of the connection channel inlet and in its thin fluid form is then also capable of penetrating into the fine branches of the mold cavity, in fact without the risk of air pockets.

Thus, it is preferred that the one or each connection channel has a diameter of 0.8 mm to 1 mm and in particular of 0.6 to 0.7 mm whereby it is appreciated that further connection channels can also just like that be provided in the muffle that do not change the inhibiting effect for viscous compounds.

Based on the fact that several press blanks are received side by side, a quite large cross-section of the pressing channel arises, whereby the transition between the pressing channel and the connection channel runs still more sudden. When pressing the molten blank material from the press blanks, the molten blank material is subjected to a shear stress as a result of the edges at the entrance or inlet to the connection channel. The shearing forces are the larger, the larger is the cross-sectional area of the pressing channel in comparison to the cross-sectional area of the connection channel. Large shearing forces lead to the fact that air pockets in the molten blank material due to compression can migrate along the grain boundaries of the material, and are thus squeezed out of the material. Thus, with the aid of a sudden transition between pressing channel and connection channel, air pockets and bubbles can be squeezed out of the the molten blank material, thus further improving the quality of the finished product.

Further, according to the invention, the molten material from the press blanks is better swirled due to the sudden transition between pressing channel and connection channel and is thus better intermixed. Based on a large cross-section of the pressing channel in combination with a small cross-section of the connection channel, a large shearing effect or stress can be generated at the transition that so to speak squeezes out air pockets.

The swirl or turbulence can be further increased by a specific surface treatment of the wall of the connection channel. Further, based on a substantially concave construction of the pressing channel when viewed from the inside that has no protruding corners and edges, the friction of the press stamp at the wall of the pressing channel is reduced. Thus, the press stamp in the pressing channel less easily jams, whereby the pressing channel not necessarily needs to have completely concave shape.

The inventive construction of the pressing channel whose cross-section matches the outer contour or external form of a multiple arrangement of flat blanks abutting on one another further provides more space in the pressing channel for receiving a large blank volume and simultaneously provides a compact construction of the muffle.

Due to the large cross-sectional area of the pressing channel a large amount of blank material can be pressed by means of a low stroke carried out by the press stamp.

At the same time, the muffle according to the invention can be employed more flexibly, since both small ceramic dental restoration components and large ceramic dental restoration components can be easily produced by means of the muffle.

The amount of dental restoration material required for production can be controlled by the number and size of the press blanks arranged in the pressing channel.

Incidentally, due to the larger difference in cross-section between pressing channel and connection channel, the lateral flow rate in the connection channel is increased. The result is a larger friction and thus a still better intermixing of the blank material.

The effect according to the invention can also be achieved with the aid of a single blank only that is employed in the large pressing channel according to the invention. Said blank fills the entire bottom surface of the large pressing channel according to the invention during the melting process, thus offering the above-mentioned advantages.

The intermixing of the blank material can be further improved in the case that the diameter of the connection channel leading from the pressing channel to the mold cavity at least partially increases, whereby an irregular surface of the connection channel can be used to further increase the turbulence.

In order to facilitate the flow of the blank material into the connection channel, said connection channel can be shaped as a funnel at its entrance. This can be achieved by a bezel, a chamfer or rounding off or any other technical measures.

In order to optimally make use of the muffle, the profile of the perimeter of the pressing channel should be adjusted to the arrangement of the blanks. The best results can be achieved if the blanks not only support each other in the pressing channel but also sit close to the wall. In the case of two round blanks this is achieved by providing an oval cross-section of the pressing channel for example. In such a pressing channel, preferably smaller gaps are provided so that a counter or back pressure that has an effect on the entrance of the connection channel, starts to build up relatively fast during the melting process.

In order to ensure an optimum stability of the muffle, the wall thickness of the muffle can amount to between half and 1.5-times the diameter of the pre-pressing chamber, in particular the single diameter.

Preferably, the pressing channel—if viewed in perimeter direction—can be free. from inward-facing edges. If the pressing channel in this case is bent edge-free in all peripheral directions, the risk that the press stamp in the pressing channel jams, is minimized.

In the muffle, the second blank can at least abut linearly on the first blank and on the wall of the pressing channel along lines that extend parallel to the axis of the pressing channel, and the second blank can two-dimensionally abut on the first blank and on the wall of the pressing channel at a surface that extends in a direction transverse to the axis of the pressing channel, the surface in particular extending in a bent manner.

The connection channel can be formed with sharp edges at its inlet from the pressing channel. The ratio between a diameter of the connection channel and a diameter of the pressing channel can be smaller than 10%, preferably smaller than 2%, and the wall thickness of the muffle can be in between 10% and 50% of its diameter, said muffle preferably having a wall thickness of approximately one third of its diameter, and the bottom thickness of the muffle can amount to between 25% and 75% of its total height, said muffle preferably having a bottom thickness of 50% of its total height.

The muffle can have a sloping face at the outside to its pressing channel side that extends over more than 10% of its height for example, in particular more than 20% of its height, and that renders the muffle more flexible at this location.

When processing press blanks, the sum of the volumes of the blanks can substantially be the same as the sum of the volumes of the connection channel and the mold cavity, and the blanks can have a cross-section that is substantially round, oval, elliptic and/or polygonal.

In a further refinement it is provided that the pressing channel is capable of receiving three press blanks.

In a further refinement it is provided that the press blanks abut linearly on one another.

In a further refinement it is provided that a cross-section of the pressing channel is substantially round, oval, elliptic or polygonal.

In a further refinement it is provided that all of the press blanks together substantially completely fill the pressing channel.

In a further refinement it is provided that a blank outer contour formed in the pressing channel by the press blanks arranged side by side, matches the cross-section of the pressing channel.

In a further refinement it is provided that the pressing channel is capable of receiving two levels or layers of at least two, in particular three press blanks each.

In a further refinement it is provided that the pressing channel is capable of receiving two levels or layers of blanks, said blanks being different in number and different in size.

In a further refinement it is provided that prior to pressing at least two press blanks are inserted into the pressing channel of the muffle side by side and preferably abutting on one another.

In a further refinement it is provided that prior to pressing three blanks are inserted into the pressing channel side by side and abutting on one another.

BRIEF DESCRIPTION OF THE FIGURES

Further advantages, details and features emerge from the following description of several exemplary embodiments based on the drawings, in which.

DETAILED DESCRIPTION

Figure 1:
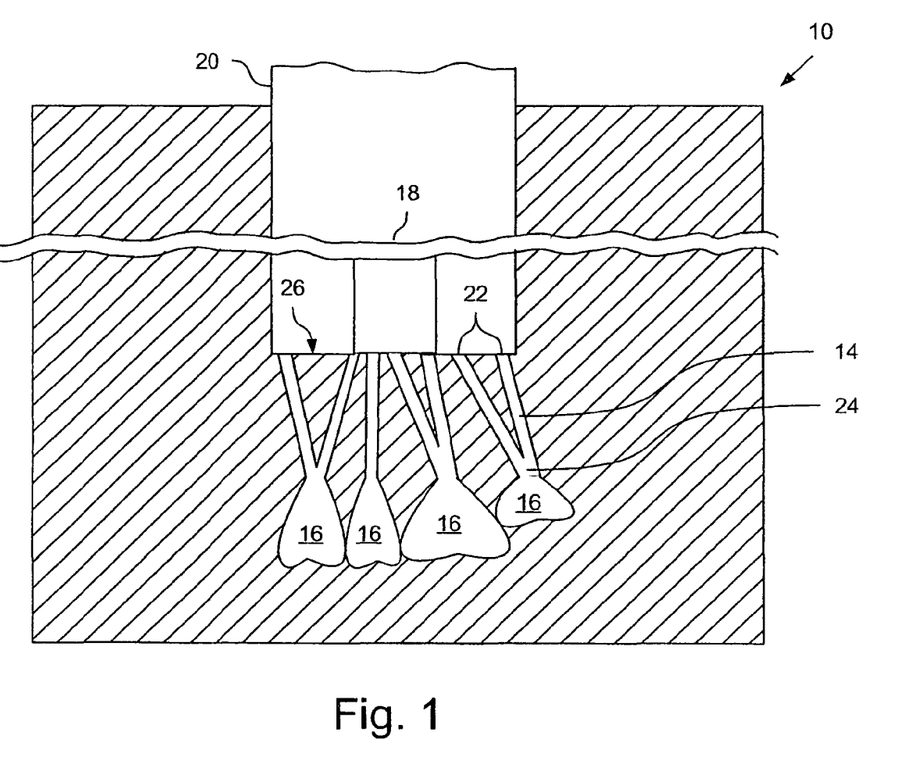
FIG. 1 shows a cross-section of a first exemplary embodiment of a muffle according to the invention with three blanks received therein and with one press stamp.

Referring to FIG. 1, the inventive muffle 10 comprises a pressing channel 12, several connection channels 14 and several mold cavities 16. Three press blanks 18 are arranged side by side in the pressing channel 12 of the muffle 10, said press blanks being pressurized with the aid of a press stamp 20.

As can be immediately seen from FIG. 1, the plurality of press blanks 18 arranged side by side, covers a large bottom surface 26 of the muffle 10. In contrast to this, the inlet apertures 22 into the connection channels 14 are considerably smaller, for example by the factor 20 or 50. Thus, the press stamp 20 has to exert a high pressure on the press blanks 18 in the pressing channel 12, in order to squeeze the molten blank material out of the press blanks 18 into the connection channels 14 and in order to overcome the resistance of the blank material to deformation. Due to the narrow inlet, the connection channels 14 act so to speak as a barrier against an insufficient free-flowing blank material that possibly still comprises air bubbles. If the material due to its fluidity or low viscosity, respectively, has been well intermixed and air bubbles have been squeezed out of the molten blank material, the material ist so thin fluid that it enters the connection channels 14. As a result, the molten blank material entering the mold cavities 16, is more homogeneous so that less cracks form upon curing the ceramic dental restoration component.

With the aid of a skillful arrangement of the connection channels 14, the intermixing of the molten material from the blanks 18 can be further improved. Effective results can already be achieved with a cross-sectional ratio between the connection channel 14 and the pressing channel 12 of approximately 1:100; the best results can be achieved with a cross-sectional ratio of approximately 1:2500.

Figure 2:
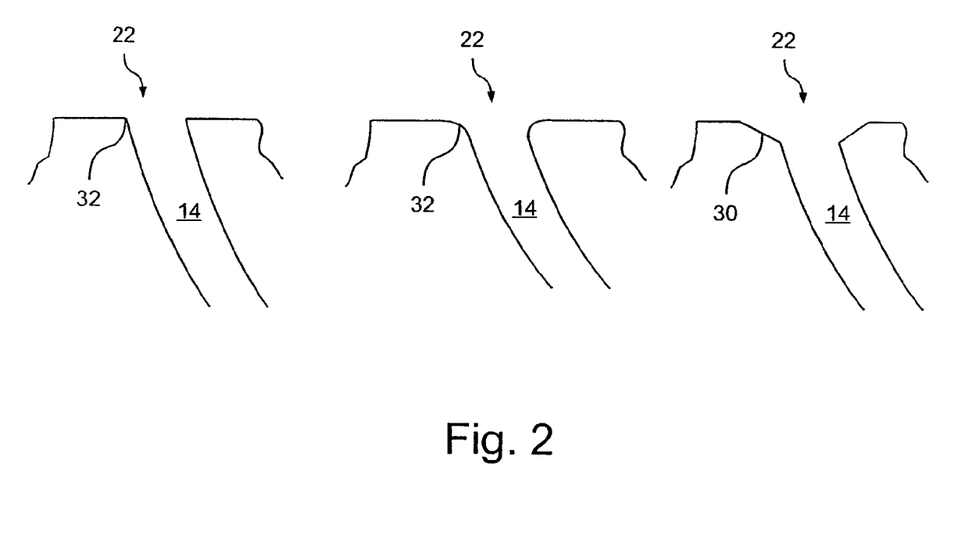
FIG. 2 shows a first to third exemplary embodiment of a connection channel within the muffle.

FIG. 2 shows measures how the turbulence of the blank material can be influenced by the inlet aperture 22.

A sudden transition between the pressing channel 12 and the connection channel 14 can be achieved with the aid of sharp edges 32 at the inlet aperture 22, thus effecting a more intensive shearing stress or effect.

Alternatively, it is possible that the inlet aperture 22 has rounded edges 28 or chamfered edges 30 between the connection channel 14 and the pressing channel 12. In this case, the inlet apertures of the individual connection channels 14 act as funnels that further compress the molten blank material. Thus, it is intended to squeeze out air pockets in the material when it enters the connection channel 14, if possible.

Figure 3:
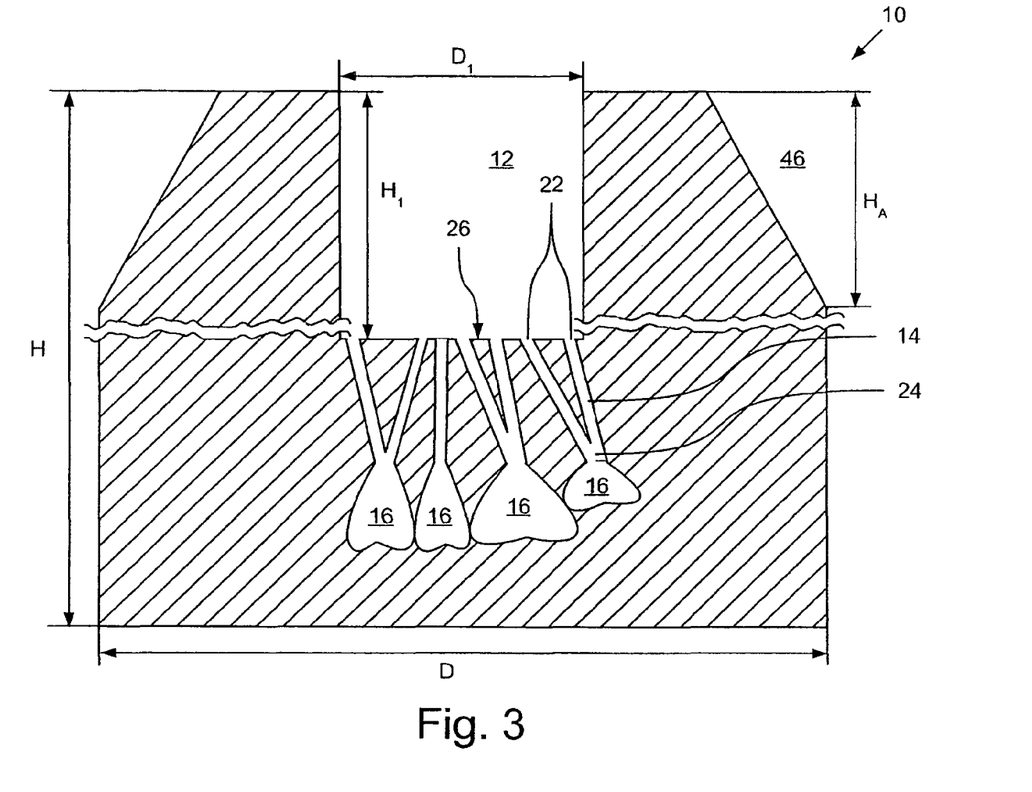
FIG. 3 shows a cross-section of a second exemplary embodiment of the muffle according to the invention.

FIG. 3 shows a further exemplary embodiment of the inventive muffle 10, however not to scale. Features that have already been discussed with reference to FIG. 1, have the same reference numerals and are not discussed once again. The muffle 10 comprises a bottom area 40 and a wall 42. The thickness of the bottom area 40 is selected such that it approximately amounts to 0.5 to 1.5 times the depth H1 of the pressing channel 12. The wall 42 of the muffle 10 is also embodied in such a manner that it has a thickness of 0.5 to 1.5 times the width of the pressing channel 12. Preferably, the thickness of the bottom area 40 is identical to the depth of the pressing channel. Similarly, the thickness of the wall 42 corresponds to the width of the pressing channel 12.

In the present exemplary embodiment, the muffle 10 comprises a sloping edge 46 whose height HA corresponds to more than 10% and preferably more than 20% of the total height H of the muffle 10, thus rendering the muffle 10 more flexible and enabling it to better absorb the stresses on the muffle material that result from pressing the press blanks 18.

Figure 4:
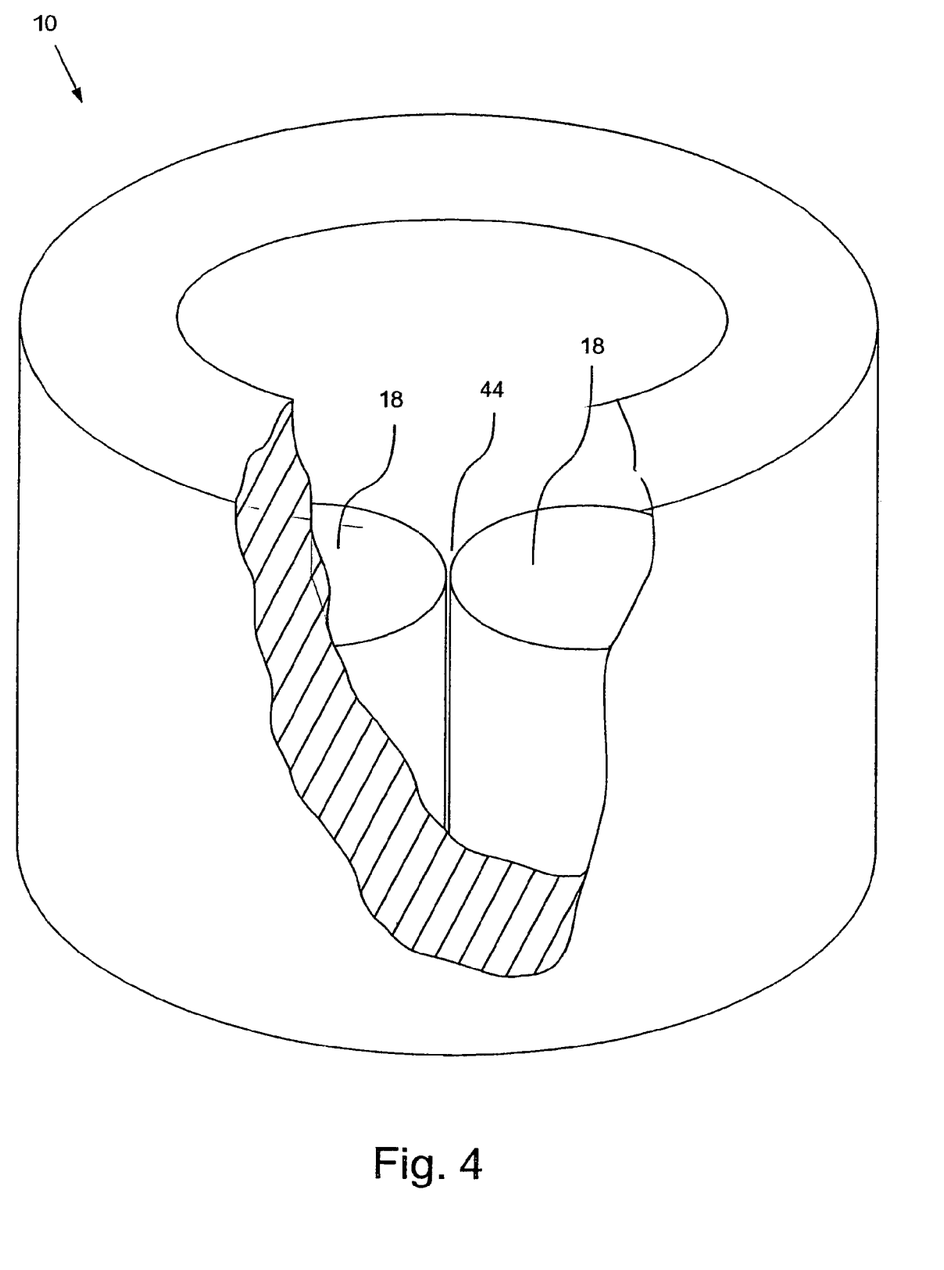
FIG. 4 shows a partially broken perspective and selective view of a third exemplary embodiment of the muffle according to the invention with blanks received therein.

As it is illustrated in FIG. 4, the pressing channel 12 of the muffle 10 in principle can be constructed to have oval shape such that two press blanks 18 can be received side by side. With a muffle of this kind, the pressing channel 12 is capable of taking or holding comparatively large amounts of blank material.

Nevertheless, the stroke required for processing the blank material to be pressed, is comparatively small such that the inventive muffle 10 can be used in a standard press oven without any problems.

Since according to FIG. 4 the pressing channel 12 of the muffle 10 is concave and is formed without points of discontinuity, it has a comparatively small periphery. This offers little working surface for the press stamp 20 such that the friction between the press stamp 20 and the wall of the pressing channel 12 ist small, and the press stamp 20 can exert a comparatively high pressure on the molten blank material.

Figure 5:
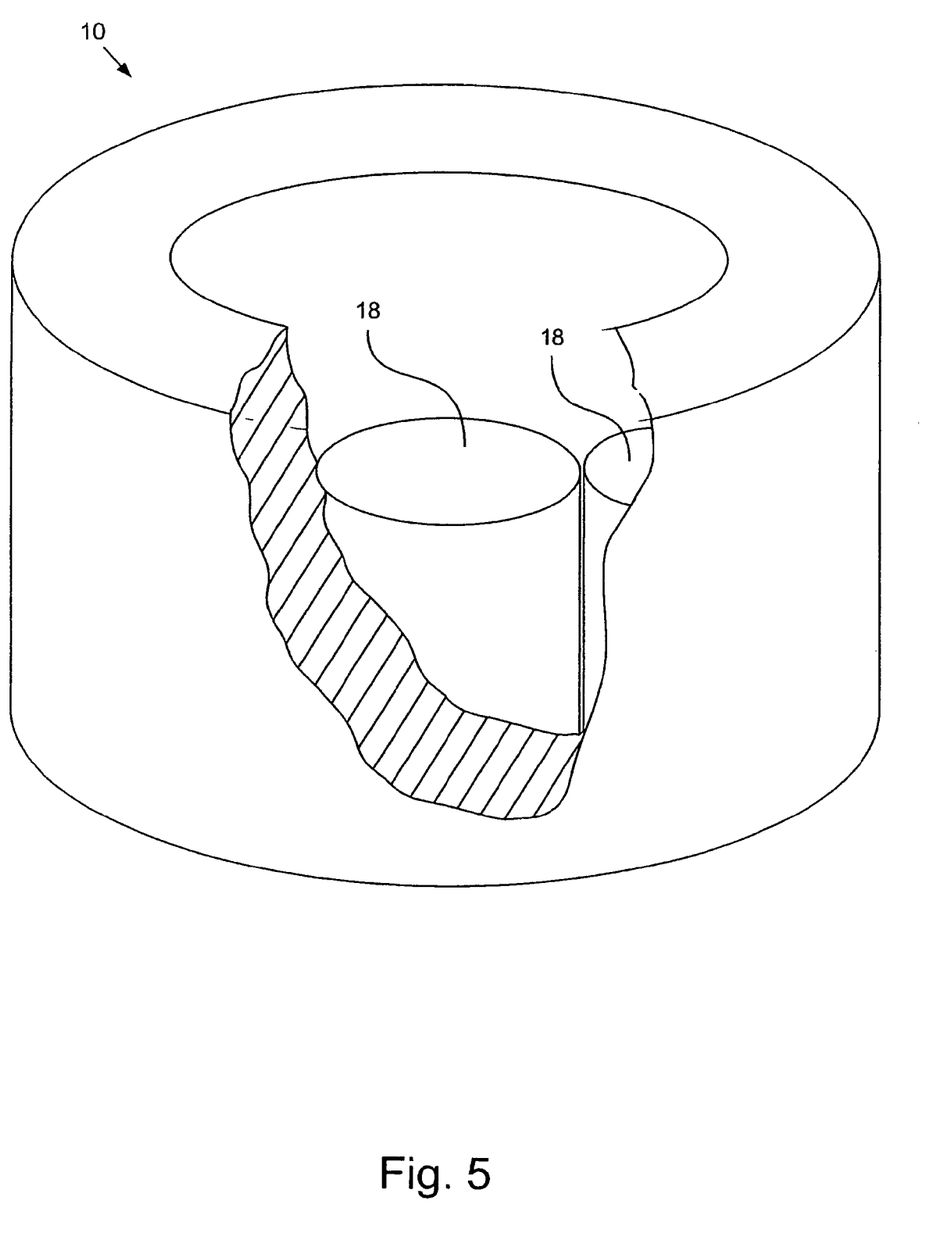
FIG. 5 shows a partially broken perspective and selective view of a fourth exemplary embodiment of the muffle according to the invention with blanks received therein.
Figure 6:
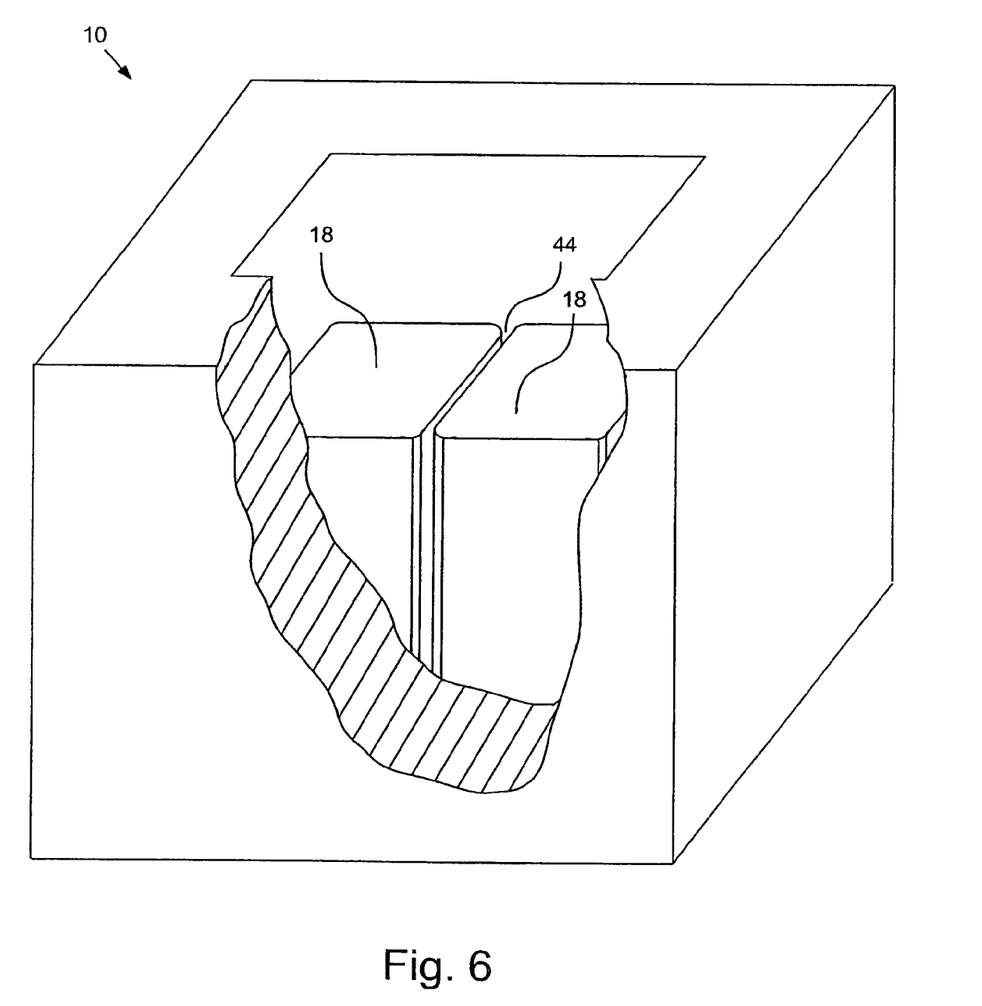
FIG. 6 shows a partially broken perspective and selective view of a fifth exemplary embodiment of the muffle according to the invention with blanks received therein.

In order to keep gaps 44 between the individual press blanks 18 as small as possible, press blanks 18 of various sizes can be used, as it is shown in FIG. 5. As a result, the processing time of the blank material in the muffle 10 is reduced and the quality of the dental restoration component to be produced is increased. The deformation of the press blank 18 by means of the press stamp 20 first leads to the filling of the gaps 44 between the press blanks 18. These gaps 44 can have an extremely small volume if the press blanks 18 according to FIG. 6 have a square cross-section, and if the pressing channel has a square construction, too.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A muffle (10), for fabrication of ceramic dental restorations comprising
    a press channel (12) for receiving two or more press blanks, the pressing channel being without any inwardly-facing edges;
    at least one form hollow space (16) connected with the press channel (12) by means of at least one connecting channel (14), the diameter of the inlet apertures (22) into the connection channels (14) being considerably smaller than the diameter of the pressing channel (12) by a factor of at least 10;
    at least two blanks (18) of cylindrical or columnar form, wherein the at least two blanks are receivable within the press channel (12), the at least two blanks being adjacent to one anther;
    characterised in that
    the at least two blanks (18) are arranged side-by-side; and
    the at least two blanks (18) together substantially completely fill-up the press channel (12).

2. A muffle as claimed in claim 1, wherein the pressing channel (12) is capable of receiving three press blanks (18).

3. A muffle as claimed in claim 1, wherein the press blanks (18) abut linearly on one another.

4. A muffle as claimed in claim 1, wherein a cross-section of the pressing channel (12) is substantially round, oval, elliptic or polygonal.

5. A muffle as claimed in claim 1, wherein a blank outer contour formed in the pressing channel (12) by the press blanks (18) arranged side by side, matches the cross-section of the pressing channel (12).

6. A muffle as claimed in claim 1, wherein the pressing channel (12) is capable of receiving two levels or layers of at least two press blanks (18) each.

7. A muffle as claimed in claim 1, wherein the pressing channel (12) is capable of receiving two levels or layers of blanks, said blanks being different in number and different in size.

8. The muffle as set forth in claim 1 wherein the ratio is about 50:1.

9. A method for producing ceramic dental restoration components comprising the following steps:
- providing a muffle with a pressing channel serving to receive two or more press blanks, the muffle having at least one form hollow space (16) connected with the press channel (12) by means of at least one connecting channel (14), the diameter of the inlet apertures (22) into the connection channels (14) being considerably smaller than the diameter of the pressing channel (12) by a factor of at least 10, the pressing channel being without any inwardly-facing edges;
- inserting at least two press blanks (18) of cylindrical or columnar form into the pressing channel (12) of the muffle (10) side by side to substantially completely fill-up the press channel;
- melting the material of the at least two press blanks; and
- pressing the melted material through the connecting channel into the at least one form hollow space (16).

10. A method as claimed in claim 9, wherein prior to pressing three blanks are inserted into the pressing channel (12) side by side and abutting on one another.

11. The method for producing ceramic dental restoration components as set forth in claim 9 wherein the ratio is about 50:1.

12. A Muffle (10) for fabrication of ceramic dental restorations comprising
- a press channel (12) having a constant cross-section for receiving press blanks;
- at least one form hollow space (16) connected with the press channel (12) by means of at least one connecting channel (14), the diameter of the inlet apertures (22) into the connection channels (14) being considerably smaller than the diameter of the pressing channel (12) by a factor of at least 10;
- a first layer of two blanks (18) received within the press channel (12), each of the blanks being of a cylindrical or columnar form;
- characterised in that
- the two blanks (18) are adjacent to one another side-by-side in an abutting manner; and
- the two blanks (18) together substantially completely fill-up the cross-section of the press channel (12).

13. The muffle as set forth in claim 12 wherein a second layer of blanks is provided, the second layer consisting of two blanks received within the press channel directly over the first layer of two blanks, the second layer of two blanks being adjacent to one another in an abutting manner and together substantially completely filling-up the cross-section of the press channel (12).

14. The muffle as set forth in claim 12 wherein the ratio is about 50:1.

15. A muffle (10), for fabrication of ceramic dental restorations comprising
- a press channel (12) having a polygonal cross-section for receiving press blanks;
- at least one form hollow space (16) connected with the press channel (12) by means of at least one connecting channel (14), the diameter of the inlet apertures (22) into the connection channels (14) being considerably smaller than the diameter of the pressing channel (12) by the factor 10 or more;
- a first layer of three blanks (18), wherein first layer of three blanks are received within the press channel (12), each of the three blanks being of a cylindrical or columnar form;
- characterised in that
- the first layer of three blanks (18) are arranged side-by-side and substantially completely filling-up the cross-section of the press channel (12).

16. The muffle as set forth in claim 15 wherein a second layer of blanks is provided, the second layer consisting of three blanks received within the press channel directly over the first layer of three blanks, the second layer of three blanks being adjacent to one another in an abutting manner and together substantially completely filling-up the cross-section of the press channel (12).

17. The muffle as set forth in claim 15 wherein the ratio is about 50:1.

* * * * *